United States Patent [19]
Balan et al.

[11] Patent Number: 5,689,115
[45] Date of Patent: Nov. 18, 1997

[54] ADVANCED NUCLEAR MEDICINE SYSTEM

[75] Inventors: Adi Balan; Gideon Berlad; Alex Fishler; Doy Maor; Alex Silberklang, all of Haifa, Israel

[73] Assignee: Elscint Ltd., Haifa, Israel

[21] Appl. No.: 562,375

[22] Filed: Nov. 24, 1995

[51] Int. Cl.⁶ .................................................. G01T 1/166
[52] U.S. Cl. ............................. 250/363.07; 364/413.24
[58] Field of Search ................................... 128/653.1, 659; 364/413.13, 413.24; 250/363.07, 363.09

[56] References Cited

U.S. PATENT DOCUMENTS

| | | |
|---|---|---|
| 3,011,057 | 11/1961 | Anger . |
| 5,276,615 | 1/1994 | Edmond et al. . |
| 5,285,072 | 2/1994 | Klingenbeck et al. . |
| 5,293,195 | 3/1994 | Berlad et al. . |
| 5,345,082 | 9/1994 | Engdahl et al. . |
| 5,371,362 | 12/1994 | Mestais et al. . |

*Primary Examiner*—Marvin M. Lateef
*Assistant Examiner*—Derrick Fields
*Attorney, Agent, or Firm*—Greenblum & Bernstein

[57] ABSTRACT

A method of acquiring an analog electrical pulse signal caused by a radiation event impinging on a detector crystal and viewed by a plurality of detector units. An image is formed based on a plurality of the events, each of which is captured by some of the detector units. The method of acquiring includes.

(a) adding a linearity enhancement signal to the analog signal; and (b) converting the analog signal to a digital signal, where the linearity enhancement signal is slowly varying relative to the length of an analog signal pulse. Alternatively or additionally, a resolution enhancement signal is added to the analog signal before (b) converting the analog signal to a digital signal. The resolution enhancement signal varying relatively quickly compared to the length of an analog signal pulse.

35 Claims, 5 Drawing Sheets

FIG. 6

ADVANCED NUCLEAR MEDICINE SYSTEM

FIELD OF THE INVENTION

This invention is related to the art of nuclear medicine imaging and in particular to nuclear medicine systems.

BACKGROUND OF THE INVENTION

Figure 1:
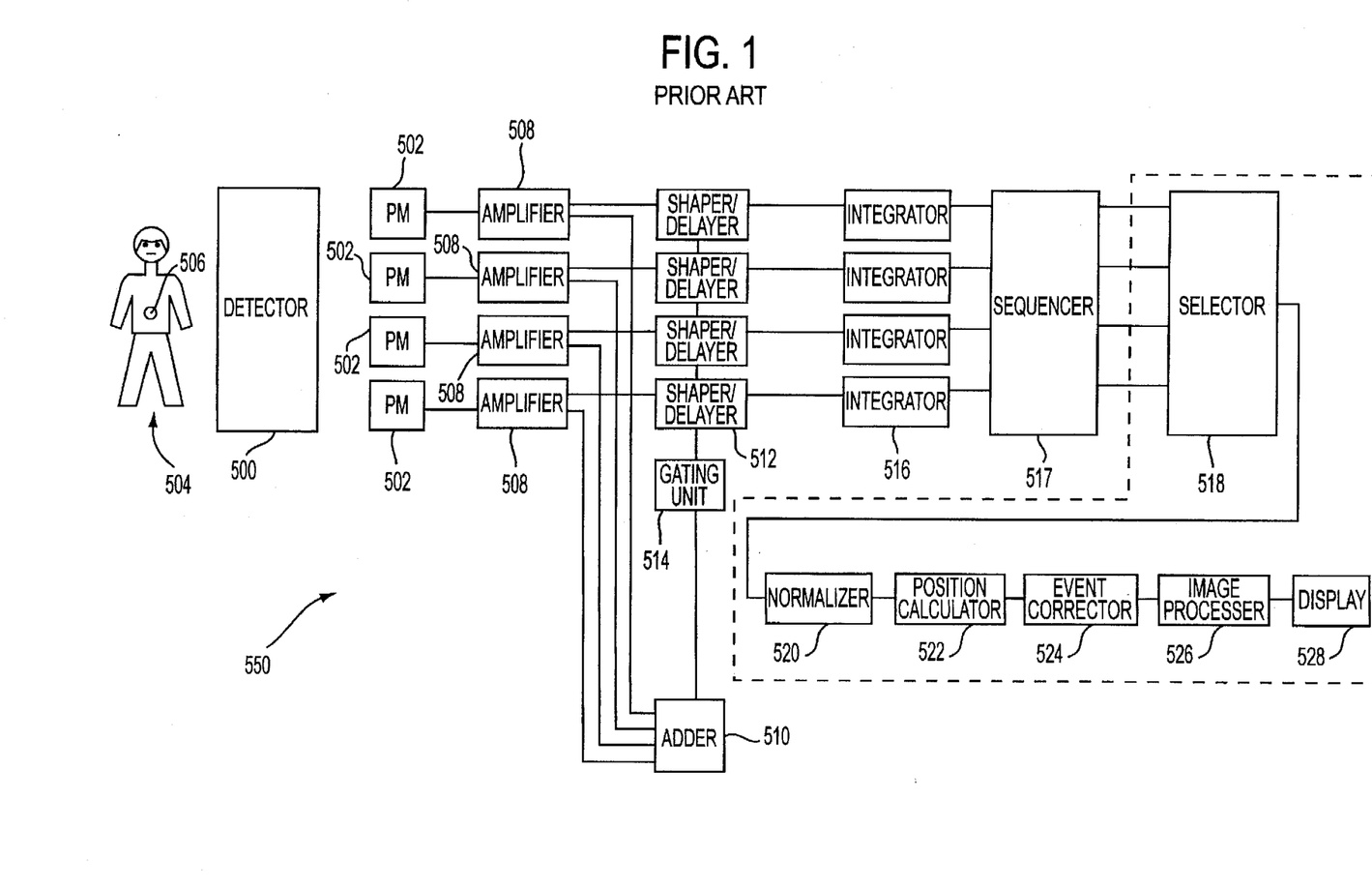
FIG. 1 is a block diagram of a prior art nuclear medicine system.

FIG. 1 shows a block diagram of a generalized prior art nuclear medicine system 550 used to image a patient 504. System 550 is used to generate images of radio-nuclide concentrations in patient 504. Patient 504 is injected with a radio-pharmaceutical which usually forms at least a concentration 506 in portions of patient's 504 anatomy. Patient 504 is placed in an examination area (not shown) so that a scintillation detector crystal 500 can detect gamma radiation emitted by radio-pharmaceuticals in concentration 506.

In X-ray imaging, the attenuation of X-rays by internal organs and bones is measured as a wave phenomenon. The amplitude of the measured wave reflects the amount of obstruction in its path. In nuclear medicine imaging, gamma rays emitted by radioactive materials are treated as a particle phenomenon. Each measured photon corresponds to one radiation event and the number of radiation events from a region reflects the concentration of the radio-active material in that region. However, the energy of the events indicates whether they have traveled directly from concentration 506 or have their origin in a different region of the anatomy and have been scattered.

As a result, nuclear medicine system design emphasizes filtering real radiation events from scattered events (whose origin is unknown). Due to the weak interaction between gamma-rays and matter and the desire to use low dosages of radioactivity, gamma-rays are not captured on film or with detectors such as used in X-ray CT system. Gamma radiation emitted by the radio-pharmaceutical interacts with detector crystal 500 to produce minuscule flashes of light. Each radiation event generates one light flash in detector 500. Several of a plurality of photomultipliers 502 detect this flash of light and generate an electrical current responsive to the intensity of light sensed by the individual photomultiplier. The contributions of photomultipliers 502 are added together to determine the amount of energy in the event and, hence, its validity. In addition, the location of the event is determined by analyzing the signals from each of photomultipliers 502.

Each photomultiplier 502 has its own signal processing circuit. The electric current produced by each photomultiplier 502 is amplified by an amplifier 508 and is then delayed and shaped by a shaper/delayer 512. The purpose of shaping the signal is to compress the signal. Most nuclear medicine systems are event triggered and event blocked. Thus, when an event is registered the system processes it and no further event can be registered or processed while the first event is being processed. Compression shortens the time extent of an event so that processing time (integration) is shorter and the maximum event rate is higher.

Typically, shaper/delayer 512 is triggered only if the radiation event has a total energy which is within a specific wide energy window. Otherwise, the measure event is probably an uninteresting scattering event and is discarded. The outputs at all of amplifiers 508 are added by an adder 510. The sum calculated by adder 510 is used by a gating unit 514 to selectably by trigger shaper/delayer 512 responsive to the sum. If the sum is within a preset range of values, gating unit 514 triggers shaper/delayer 512 to process the radiation event. It should be noted that the total energy of the event is crudely predetermined. Using the delay, full scale integration eventually starts only if the approximate energy falls with in predefined limits.

An integrator 516 integrates the signal produced by shaper/delayer 512 to find the total energy associated with the radiation event by one specific photomultiplier 502. An important result of the integration is noise reduction. As in many measurement systems, even when there is no event being measured, there is a parasitical DC level, usually referred to as a base-line voltage. This base-line voltage is typically subtracted from the signal before integration. Otherwise the integrated signal contains a large (unknown) portion from the base-line. This process is called base line restoration.

The individual detector circuits are connected to a single event processing unit 519. To unite the circuits, a sequencer 517 sequences the results from all of integrators 516 and passes them serially to event processing unit 519.

Typically, the analog signal is converted to a digital signal after integration. Conversion of analog signals to digital signals is problematic for the short pulse durations typical of nuclear medicine imaging. In particular, analog to digital converters tend to:

(a) have relatively low resolutions;

(b) be non-linear in their response; and (c) have response curves which vary between converters and in a single converter with time.

U.S. Pat. No. 5,371,362 discloses a base line measurement and correction system. The output signals of each photomultiplier are sampled by an analog-to-digital (A/D) converter and analyzed to determine the values of the base-Line voltage between radiation events. The determined base line voltage is subtracted from the sampled signals to yield base-line corrected signals. Also disclosed, is the addition of a sliding scale voltage to the photomultiplier output signal. A sliding scale voltage is generated by the system responsive to the amplitude of the sampled signal. The sliding-scale voltage is added to the signal from the photomultipliers so that its amplitude is within the linear range of the analog to digital converter.

Figure 2A:
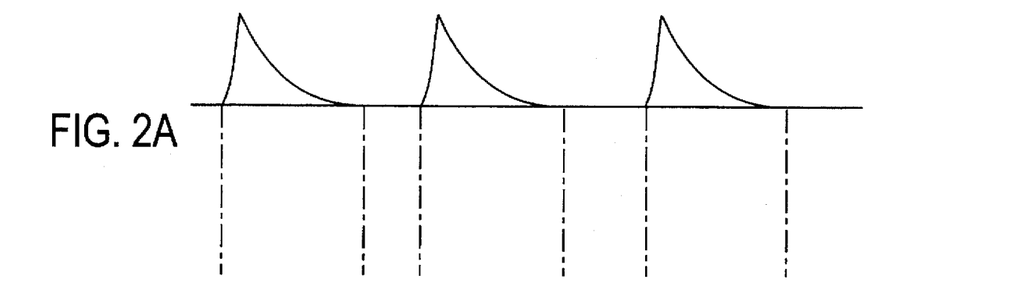
FIG. 2A is a graph showing a response of a photomultiplier tube to a series at radiation events.
Figure 2B:
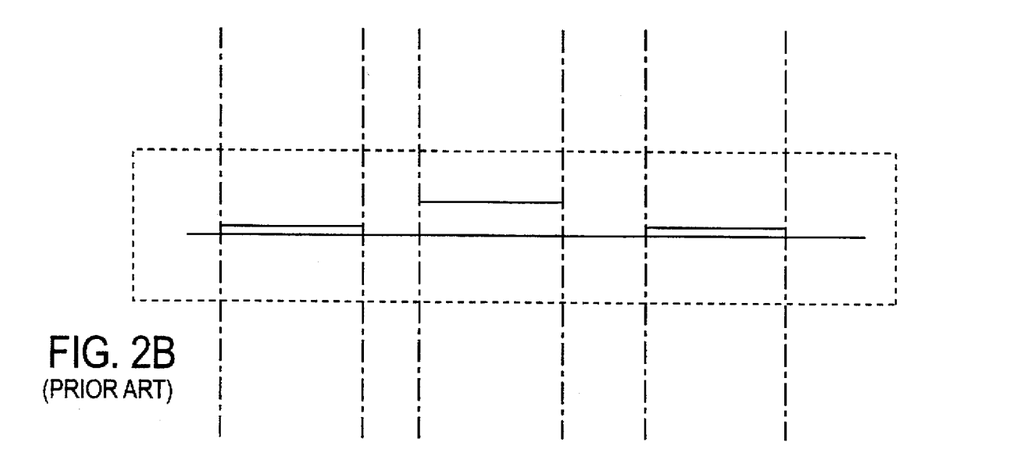
FIG. 2B abates a prior art wave form which is added to the photomultiplier response.

In the APEX system, a sliding scale signal having a cycle time which is 64 events long is added to the analog signal before conversion. The sliding scale is event driven, thus, the sliding scale signal is constant for the duration of each event and varies by one level between events. FIG. 2A shows an analog signal generated by photomultiplier tubes 502 and FIG. 2B shows a sliding scale signal as described herein. Since the cycle of the sliding scale signal is only 64 events long, the average contribution of the sliding scale signal is zero over long periods of time (and 64 events).

Referring again to FIG. 1, event processing starts with determining the X-Y position of the radiation event on detector head 500. Only strong signals are useful or this determination. Thus, a selector 518 selects only those integration results which are above a threshold. A normalizer 520 normalizes the selected results to make their sum a constant and a position calculator 522 uses the normalized results to perform Anger arithmetic and calculate the position of the radiation event in the plane of detector 500.

Typically, some of the Anger arithmetic calculations are performed by an array of weighted resistors. These resistors are connected directly to photomultipliers 502 and calculate weighted sums of the signals from photomultipliers 102.

Following positioning, the radiation events are corrected for linearity errors, energy errors and variable sensitivity errors by an event corrector 524. Linearity errors are systematic errors in the position calculation by Anger arithmetic. Sensitivity errors are caused by detector 500 having a position dependent sensitivity, i.e., some portions of detector 500 naturally detect more events than others portions, even if all of detector 500 is receiving a uniform event flux. Energy errors are caused by non-detection of some of the Light generated by an event, e.g., light passing through the spaces between photomultiplier tubes 502. Thus, similar events are acquired by system 550 as having dissimilar energy levels. Usually, the events whose energy level is not within a position dependent narrow window are rejected by system 550. In some nuclear medicine systems, events are corrected only after non-events are rejected.

If it is desired to transform the image, (e.g., enlarging it), there are two possible solutions. Corrector 524 can be configured to perform the transformation. However, all of the geometric transformations (linearity corrections and others) are usually performed as one step using a single table. Thus, when the desired transformation changes, the geometric transformation table in corrector 524 must be recalculated, which is time consuming.

Alternatively, the transformations can be performed on the final image. However, the quality of the transformed image is lower than the quality of the original image, due to aliasing effects.

Image generation by an image processor 526 completes the processing of radiation events so that a completed image can be displayed on a display 528.

U.S. Pat. No. 5,345,082 discloses energy dependent linearity correction. A separate linearity correction map is stored for each of several energy ranges. The positioning of a detected event is corrected using the linearity map which matches the event's energy.

U.S. Pat. No. 5,276,615 mentions a nuclear medicine system wherein the outputs of the photomultiplier tubes are directly sampled by an analog-to-digital converter. Apparently, summing, integration and positioning are performed digitally on the sampled outputs.

SUMMARY OF THE INVENTION

It is an object of the present invention to provide a nuclear imaging system having improved image quality. According to a preferred embodiment of the invention, a digital nuclear medicine system includes, a detector unit which generates an analog electrical signal responsive to an impinging radiation event. The analog signal is converted to a digital signal before any steps of (a) integrating the signal to provide an energy value for the event; or (b) summing analog signals from a plurality of detectors.

After conversion, the digital signal is baseline restored and the signal is integrated to provide an energy value for the event.

In general, digital processing of signals is faster, more stable, precise and flexible than processing analog signals. Nuclear medicine systems are signal processing intensive, thus, a digital processing system is advantageous. However the step of converting analog signals to their digital counterparts usually degrades the signal resolution and adds noise. As a result, prior art nuclear medicine systems optimize their image quality by postponing the A/D conversion until after at least some of the processing is performed using analog circuitry.

Analog to digital conversion has a limited resolution, however, this resolution can be enhanced by varying the input signal. For example, if a constant signal having the value of 2.9 is converted by an analog to digital converter having the resolution of 1, the resulting digital value will be 2, an error of approximately 50%. However, if a periodic signal having the amplitude of 1 is added to the analog signal, the resulting analog value will cycle between 1.9 and 3.9. If this new signal is sampled and converted several times, the average digital signal will be approximately 2.9.

In a first preferred embodiment of the present invention, a resolution enhancement signal is added to the analog signal before converting the analog signal to the digital signal. Preferably, the resolution enhancement signal is a time varying cycle or pseudo-random signal which cycles several times during the detection of a single event and has a precision higher than the resolution of the analog to digital converter. More preferably, the resolution enhancement signal has an amplitude on the order of the resolution of the analog to digital conversion. Preferably, the sum of the resolution enhancement signal over one integration time is zero. Thus, the resolution enhancement signal does not add noise to the integrated signal and, as a consequence, does not need to be corrected for before integration. In a further preferred embodiment, especially useful when the integration time of the digital signal is not constant, the addition of the resolution enhancement signal is corrected for by subtracting a digital equivalent of the resolution enhancement signal from the digital signal before restoring the baseline.

The resolution enhancement signal is preferably synchronized to the analog to digital conversion process.

A second limitation of analog to digital converters is that they are not uniformly linear over their acquisition range. These non-uniformities can be corrected by mapping the response of the converter and correcting some of the errors after acquisition. However, even if a converter is mapped to correct for these non-uniformities, when the converter is replaced it must be mapped again. In addition, the linearity of analog-to-digital converters changes over time.

Thus, in a second preferred embodiment of the invention, a linearity enhancement signal is added to the analog signal before conversion thereof to the digital signal. The linearity enhancement signal is added in addition to, or alternatively to, the resolution enhancement signal. Preferably, the linearity enhancement signal cycles slowly, such that it approximates a constant signal during the integration time of a single event. Also, the amplitude of the linearity enhancement signal is preferably approximately 5% of the range of the analog to digital converter. The precision of the linearity enhancement signal is preferably higher than the resolution of the analog to digital converter. Optionally, a digital equivalent of the linearity enhancement signal is subtracted from the digital signal before base line restoration.

It should be appreciated that the digital signal that has its base line restored by the base line restorator has a higher precision than the digital signal generated by the analog to digital converter. It should also be appreciated that since the linearity enhancement signal varies slowly, the base line restorator treats it as a DC signal so that the base line restorator can adapt to the linearity enhancement signal without special circuitry and without receiving the linearity enhancement signal as an input.

In order to generate an image based on a plurality of radiation events, several steps are preferably performed on each event:

(a) the location of the radiation event is determined;

(b) linearity errors in the positioning of the event are corrected;

(c) errors in the determination of the energy of the event are corrected;

(d) errors in event detection are corrected, for example, errors due to non-uniform sensitivity of the detector;

(e) other positioning errors in this positioning of the event are corrected, for example, errors caused by mechanical misalignment;

(f) the position of the event is transformed using a general geometric transformation, for example, zooming in; and (g) events are assigned to a location in an image plane. Generally, when more than one of (b), (e) and (f) are performed, they are usually performed using a single transformation map. Alternatively, (e) or (f) are performed on the image plane after (g).

This method has several disadvantages. First, it is time consuming to calculate the single transformation map. Thus, when any of the corrections or transformations in (b), (e) or (f) are changed, the entire nuclear medicine system is paused until the recalculation is finished. Second, corrections which are time dependent are impossible to perform, since the transformation map is static and the image plane has no time dimension. Third, if a correction is applied to the image matrix, the result is only as precise as the resolution of the image plain, which is clinically 6–8 bits and does not usually exceed 10 bits.

In a preferred embodiment of the invention, (a)–(f) are performed as separate, independent steps on each individual event. Thus, an event is assigned to the image plane only after all the desired transformations and corrections have been applied to it. As a result, each event can have different, non-constant, possibly time based, corrections and transformations applied to it. In addition, the precision of (a)–(a) is as great as the calculation system, not limited by the image plane resolution.

A preferred time-based correction, corrects for distortions caused by some radio-pharmaceuticals deteriorating rapidly during a nuclear medicine session. Radiation events which occur later in the session are given higher weights to compensate for this deterioration.

Another preferred non-constant correction is a correction for mechanical misalignment. In a typical tomographic nuclear medicine system, detector assemblies are rotated around a patient. However, the detector assemblies sag as a result of their weight. Also, the center of rotation for the assemblies is not always exactly at the center of the projection plane. In a preferred embodiment of the invention, the error in the position of the event caused by sagging of the camera detectors is corrected by applying an angle based geometric transformation to each event. The center of rotation is also corrected by applying a second geometric transformation to the event. These corrections can be combined in a single geometric transformation Yet another preferred non-constant correction is a velocity correction for linear scanning, where a detector scans along the patients body. In a preferred embodiment of the present invention, velocity changes are corrected for by giving each event a position dependent weight, depending on the velocity of the detector at that position.

A preferred geometrical transformation is converting a fan beam image to a parallel beam image to optimally utilize both detector and image plane area. In a preferred embodiment of the present invention, a small portion of the patients body is imaged using a fan-beam collimator. However, the radiation events are repositioned, before being assigned to the image plane, to simulate the use of a parallel beam collimator. Thus, a high resolution fan-beam image is displayed without the typical distortions caused by the fan beam collimator.

Since each event is provided with a weight, several type of irregularities are correctable by varying the weighting of each event. Sensitivity correction is achieved in a preferred embodiment of the present invention by first mapping the sensitivity uniformity of the detector and, during acquisition, giving each event a (fractional) weight which is dependent on the event's position in the detector.

If radiation events happen faster than the nuclear medicine system can handle, the events are lost. In a preferred embodiment of the present invention, an event counter counts the number of actual events. A higher weight is attached to an event arriving from a patient location which lost events due to a high number of events from that location.

In another preferred embodiment, events occurring during a short frame are given a higher weight than events occurring during long frame times. Thus, images having different frame times but similar content, will have similar intensities.

DETAILED DESCRIPTION OF THE PREFERRED EMBODIMENTS

Figure 3:
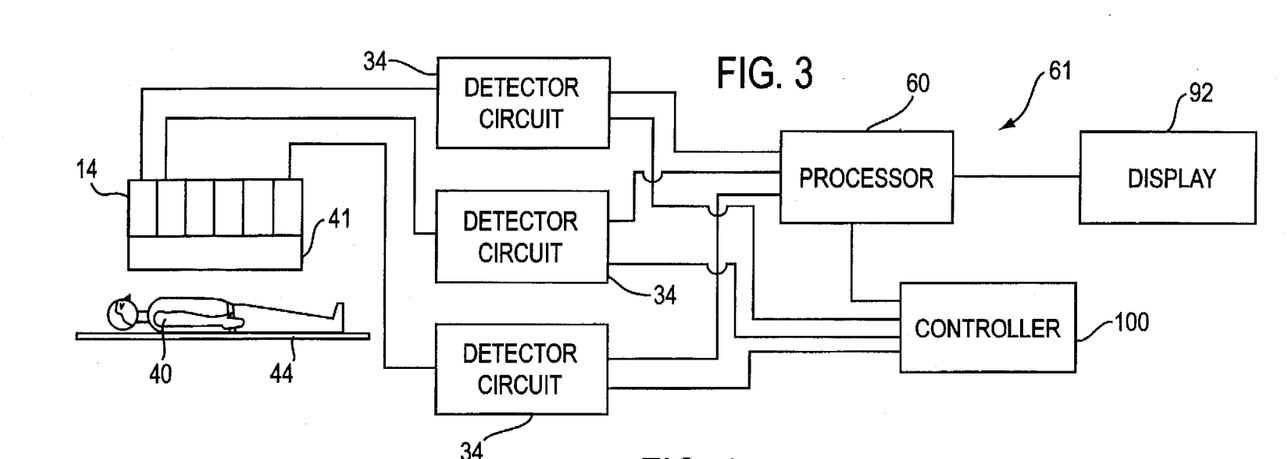
FIG. 3 is a general block diagram of a nuclear medicine imaging system according to a preferred embodiment of the invention.

FIG. 3 is a general schematic of a nuclear medicine system 61 according to a preferred embodiment of the invention. System 61 generally comprises an examination area 44, a detector crystal 41 and a plurality of photomultiplier (PM) tubes 14. When a gamma-ray source is placed in examination area 44, gamma-rays created by a radiation event interact with detector 41 to generate weak scintillations. These scintillations are amplified by PM tubes 14, which also convert the scintillations into electrical signals having an amplitude related to the energy of the interacting gamma-ray. Each of PM tubes 14 is connected to a detector circuit 34, described more fully below. The outputs from circuits 34 are passed to a processor 60 which determines the position of each radiation event from the signals generated in PM tubes 14 and combines these events to form an image. This resulting image is displayed on a display 92. System 61 is generally controlled by a controller 100 which generates controlling and timing signals.

In a typical process of nuclear medicine image acquisition, a patient 40 is injected with or ingests a radio-pharmaceutical and is placed in examination area 44. The radio-pharmaceutical is selectably absorbed by tissues in patient's 40 body, the amount of absorption being typically dependent on the metabolic processes occurring in the tissues. Decay of the radio-pharmaceutical causes a multiplicity of radiation events which are detected by detector 41. A flash of light generated in detector 41 by each detected event is acquired and amplified by at least one, and typically several, PM tube 14. The signal produced by PM 14 in response to an event is called a pulse signal. The integral of the pulse corresponds to the number of photons detected by PM 14, which in rim corresponds to the energy detected by detector 41. Detector 41 may be rotated around the portion of patient 40 that is being imaged so that a tomographical image can be generated.

Figure 4:
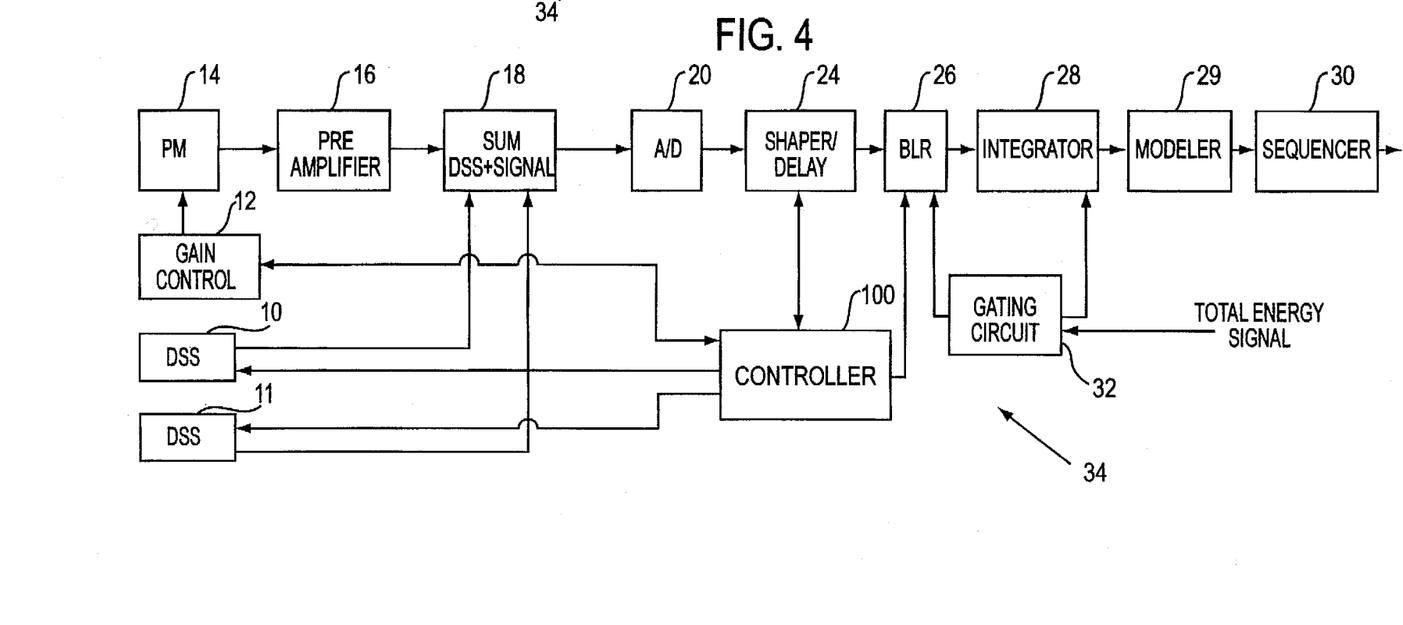
FIG. 4 is a detailed block diagram of a detector circuit of the system shown in FIG. 3.

FIG. 4 show a block diagram of detector circuit 34 according to a preferred embodiment of the present invention. The gain of each PM 14 is controlled by a gain controller 12, since each PM typically amplifies incident light by a different factor. Preferably, gain controller 12 is controlled by controller 100 to compensate for known deviations in the amplification of PMs 14. The pulse signal is preferably further amplified by a pre-amplifier 16. Preferably, pre-amplifier 16 has a small amount of smoothing to reduce noise. Typically pre-amplifier 16 has a bandwidth of 5–8 MHz. The smoothed pulse signal is digitized by an A/D converter 20. It should be noted that A/D converter 20 acquires several data samples during each radiation event, so that the pulse signal can be reproduced from the digitized data. Preferably, A/D converter 20 samples at a rate of 20 MHz. The resolution of A/D convertor 20 is preferably at least 8 bits, and most preferably 10 bits or more.

Figure 2C:
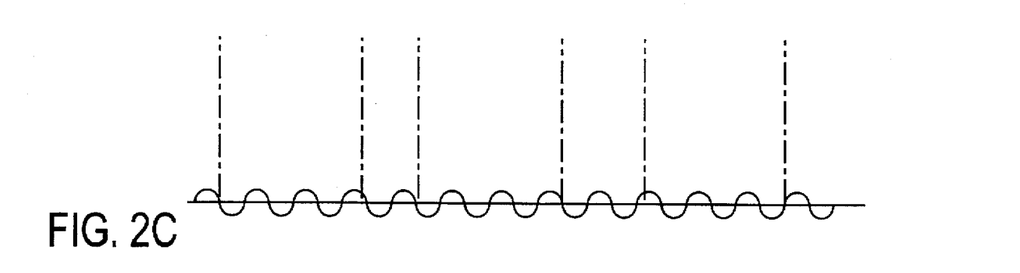
FIG. 2C–2D are graphs showing various wave forms which are added to the photomultiplier response in various preferred embodiments of the present invention.

The limited resolution of A/D convertor 20 can significantly affect the image quality. In a preferred embodiment of the present invention, a resolution enhancement signal is added to the analog signal using an adder 18. FIG. 2A shows a series of analog signals generated by a PM in response to radiation events. FIG. 2C, which shares the same time scale as FIG. 2A, shows a preferred resolution enhancement signal.

The effect of the resolution enhancement signal is best explained by the example of the acquisition of a constant signal. For example, one bit step of A/D converter 20 is equal to 8 millivolts. If a constant signal of 15 millivolts is digitized, the digitized signal has the value 1, even though the real equivalent digital value is 1.875, since only the "whole" portion of the signal is digitized. If the constant signal is dithered by a periodic signal with an amplitude of 8 millivolts (one bit), the resulting analog signal is between 7 and 23 millivolt. As a result, the digitized signal is either 1 or 2. If the dithered signal is digitized an infinite number of times, the average digital signal will approach 1.375, since in 7/16 of the cases the signal voltage will be above 16 millivolts and in 9/16 between 8 and 16 millivolts. 0.5 (half a bit) is added to the average signal to reflect the average rounding error of the A/D, i.e., the fact that all values between 8 and 15 millivolts are digitized as 1, even though their average value is 1.5.

Thus, the average acquired value is 1.875. In general, if the signal is digitized a finite number N times, the additional resolution of the digitization is log(N), if, each digitization is performed at a different phase of the dithering periodic signal.

In a preferred embodiment of the present invention, the dithering periodic signal cycles approximately two times during a pulse signal, which is approximately 800 ns.

Preferably, the periodic signal is synchronized to the digitization clock, to ensure that each digitization is at a different phase of the periodic signal. For example, if two added bits of resolution are desired, the digitization frequency is set to be four times the frequency of the periodic signal. The timing of the digitization is set so that within each cycle of the periodic signal, each digitization is at a different phase of the periodic signal. This timing repeats in consecutive signal cycles. Alternatively, a timing scheme which repeats less often is used.

The resolution enhancement effect may not be achieved for a single pulse signal, especially if the frequency of the resolution enhancement signal is low compared to the pulse signal. For example, if the resolution enhancement signal cycles only once, and there are two A/D samples in an event, the first sample may be elevated from 1.9 to 2.1, i.e, from 1 to 2) and the second sample reduced from 1.3 to 1.1 (i.e., not affected). Thus, the total detected energy is 2+(0.5)+1+(0.5) =4.0, compared to the uncorrected value of 1+(0.5)+1+(0.5) =3 and compared to the correct value of 1.9+1.3=3.2, a definite loss of accuracy.

However, even if the precision of a single digitization sample is slightly retarded, the cumulative effect on many digitized pulse signals yields a higher accuracy of measurement. It should be appreciated that when the frequency of the periodic signal is higher, in conjunction with a digitization rate as described above, the precision of digitizing a single pulse signal is higher too.

Preferably, the periodic signal is also synchronized to the integration. For example, the integration time of a pulse signal is an integral multiple of the period of the resolution enhancement signal, to ensure that the sum of contributions of the periodic signal to the integrated value is zero. However, if a variable integration time is used, the digital value of the dither signal at the sample points is preferably subtracted from the digitized signal, as described below. A useful embodiment of such a periodic wave form is a saw tooth wave.

Since all the calculations after the analog to digital conversion are digital, subtraction of the dither signal can take place before the base-restoration, by correcting each signal, or even after the integration, by subtracting the sum of the dither signal at the sample points from the integrated value. Preferably, he value of the dither signal at the sample points is known and does not need to be acquired, since the dither signal is synchronized to the digitization. Additionally or alternatively, the dither signal is controlled by controller 100, as described below.

In a preferred embodiment of the invention, the dithering signal is produced by a digital sliding scale source 10. Preferably, control and timing signals for digital sliding scale source 10 are generated by controller 100. The amplitude of the dithering signal is preferably at least as high as a resolution step of the A/D converter 20. The accuracy of the dithering signal is preferably higher than the desired additional resolution.

A/D converters do not usually have a linear response over their entire dynamic range. In addition, the linearity of A/D converters changes over time, particularly if the converter is replaced. Some analog to digital conversion systems use a linearity map to correct these non-linearities. However, using a linearity map lowers the accuracy of the digitized signal, In addition, the map needs to be updated periodically, especially if the A/D converter is replaced.

Figure 2D:
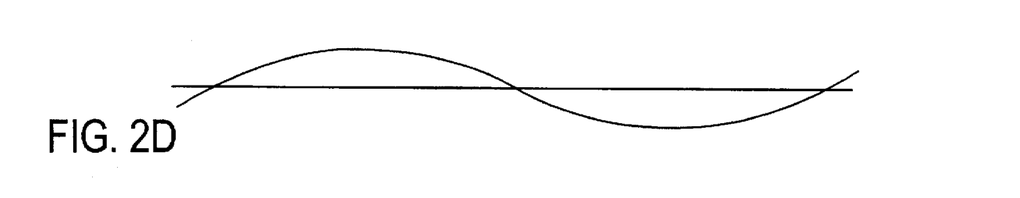

FIG. 2D shows a linearity enhancement signal (not to scale.) which is preferably added to the analog signal before digitization. This linearity enhancement signal preferably has a much lower frequency than the resolution enhancement signal, typically 60–100 Hz. The amplitude of the linearity enhancement signal is preferably about 5% of the total range of A/D converter 20. Thus, each radiation event response is digitized in a slightly different region of the dynamic range of A/D converter 20 and non-linearities are averaged out. Because the linearity enhancement signal changes very slowly compared to the duration of a radiation event response, it is perceived as a DC signal by the rest of detector circuit 34.

In a preferred embodiment of the present invention, the linearity enhancement signal is generated by a digital sliding scale source 11 and added to the analog signal by adder 18. The control and timing signal for each digital sliding scale source 11 are preferably generated by controller 100.

Preferably, each detector circuit 34 has its own digital sliding scale source 11 and these sources are not synchronized between different detector circuits. Preferably, each detector circuit 34 also has its own, unsynchronized digital sliding scale source 10. Embodiments of the invention may employ one or both types of enhancement signals.

In a further preferred embodiment of the present invention, the digital value of the resolution enhancement signal and/or the linearity enhancement signal is subtracted from the digitized signal to lower noise levels in the digitized signal. However, the subtraction is typically not needed.

Since, as described below, the base line of the signal is measured during times when no radiation event is detected, the accuracy of the measured base line is also enhanced by the resolution enhancement signal. The linearity enhancement signal does not generally add to the accuracy of the measured base line, since it adds a constant to the real base line. This constant may have an amplitude lower than the resolution of converter 20, and thus, be unknown. However, since the base line signal is continuously updated, the slowly changing linearity enhancement signal acts like part of the real base line. It should be appreciated that the accuracy of the baseline estimation is aided by the resolution enhancement signal and the linearity enhancement signal.

In a typical nuclear medicine system, only one radiation event can be processed at a time. It is therefore advantageous to shorten the processing time of a radiation event. However, the quality of the resulting image is directly proportional to the integration time of the PM signal. Thus, a shaper-delayer 24 reshapes the digital signal, after it is sampled, to produce a new digital signal with an equivalent energy, but a shorter temporal extent. In affect, the signal is compressed. Preferably, shaper-delayer 24 is controllable by controller 100 to adjustably shape pulses in a parametric manner. Thus, optionally, pulses may be shaped differently as a function of event rate. The use of adjustable pulse shaping, improves time resolution and, therefore, higher count rates are possible. It should be noted that although analog shaper-delayers are known in the art, the present invention preferably uses a digital filter to shape/delay.

Before integrating the digital signal to determine the total energy detected by an individual PM 14, it is important to subtract the baseline component of the signal. This baseline is generally equal to the DC signal detected when no events (or scattering events) are occurring, i.e., between pulse signals. Otherwise, a significant proportion of the integrated signal will be from the baseline (noise) component and not the pulse component. A base line restorator 26 is used to remove base-line components from the digital signal. Optionally, base line rastorator 28 uses inputs from controller 100 to determine he digital value of the resolution enhancement signal and the linearity enhancement signal so that they can also be subtracted from the digital signal. In general, these signals do not need to be subtracted, except as described above. However it has been found that subtracting these values yield a slightly higher accuracy for the integration.

Base line restorator 26 uses a running average scheme to continuously update the bass line, i.e., B(t)=(1/m)*((m–1)*B(t–dt) +Signal (t)), where B(t) is the baseline at time t, dt is the sampling time and Signal(t) is the input to restorator 26 at time t. Preferably, m, the number of samples, is 256. Alternatively, a moving window scheme is used, i.e., B(t)·B(t–dt)+(1/n)*(Signal(t)–Signal(t–n*dt)), where n is the window size.

A gating circuit 32 determines when no radiation events are occurring. Digital signals acquired while no radiation event response is in progress are entered into the window to estimate the base line for signals acquired while a radiation event response is in progress.

An integrator 28 is activated by gating circuit 32 to integrate (sum) digital signals acquired during a radiation event response. When the radiation event response is over (also determined by gating circuit 32), the integrated signal represents the total amount of energy from the radiation event detected by PM 14.

Gating circuit 32 is used to differentiate signals which are responses to radiation events from random noise signals and scattered radiation events. Typically, it the sum of the detected signals from all PMs 14 is outside a specific energy window, the signal is discarded as unusable. Otherwise, it is treated as a valid event, until the next filtering step. The sum is determined by adding the pulse signals from all of PMs 14, smoothing the resultant meta-pulse and searching for a peak value, which is compared to the energy window. Preferably the extent of the energy window is controlled by controller 100 in response to system noise levels, radio-pharmaceutical type and count rate.

Figures 5, 6:
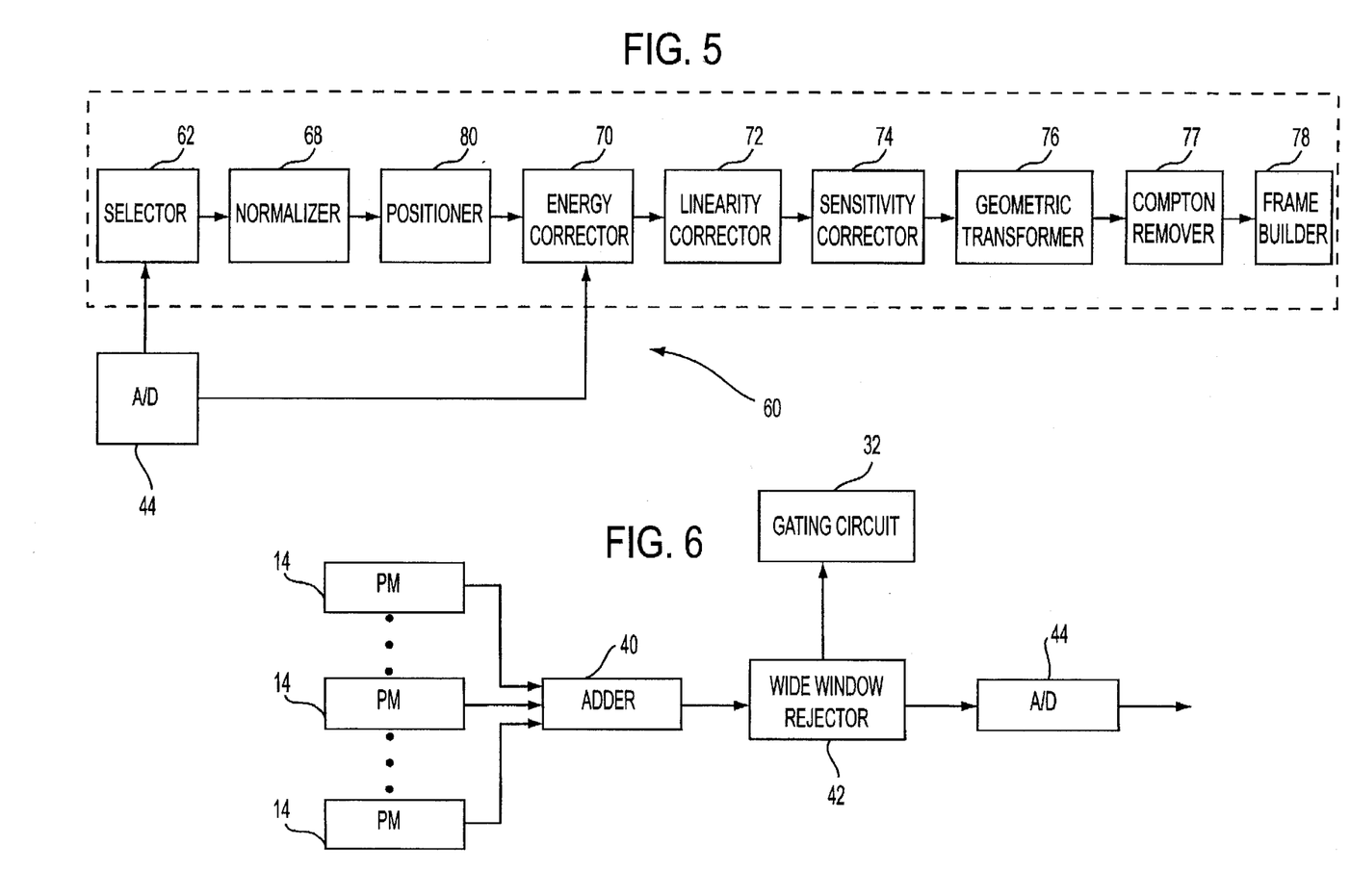
FIG. 5 is a detailed block diagram of a processor of the system shown in FIG. 3.
FIG. 6 is a detailed block diagram of gating circuit of the system shown in FIG. 4.

FIG. 6 shows a preferred embodiment of a complete gating apparatus, including an adder 40 which sums the energy readings from all of PMs 14. A wide window rejector 42 smoothes the sum (which is a continuous signal), and determines whether the energy sum has a peak within a window. If the peak is within the window, rejector 42 sends an activation signal to gating circuit 32, which is timed to start the integration and the shaping, so that they start at the beginning of the pulse signal and end at its end. It should be noted that the pulse signal is delayed by the delayer portion of shaper/delayer 24. Preferably, adder 40 sums analog signals, since analog summation is generally more precise than digital summation. The sum is then digitized by an A/D 44 for further use. Alternatively, the analog signals are digitized before being summed or before being passed to wide window rejector 42, preferably using the resolution and/or linearity enhancement signals as described above.

In an ideal system, the integrated signal has a linear relationship to the distance of the radiation event from the center of PM 14. However, in real nuclear medicine systems this relationship is distorted. A main cause of distortion is that PM 14 is more sensitive at its center than near its edges. Other causes include the difference in refractive index between detector crystal 41 and PM 14 and location dependent variations in detector 41.

Referring again to FIG. 4, in a preferred embodiment of the present invention, the spatial response of PM 14 is modeled by a modeler 29 to correct distortions. The integrated signal is corrected to reflect the value that would have been acquired had PM 14 been optimal. Preferably, all the PMs 14 are modeled using a single empirical (measured) model, usually a look-up-table, preferably one dimensional.

Alternatively, a mathematical function is used instead of a look-up-table. Alternatively, the correction model may be two dimensional. Additionally or alternatively, each PM 14 can have a different, personalized, model associated therewith.

Preferably, PM modeling is performed in detection circuit 34 by comparing a measured PMC(x,y) to an ideal value PMC(0,0), wherein PMC(x,y) is the response of the tube at to an event which occurs at location Cx,y). A look-up table is used to determine d/D, the ratio between the distance of the event from the PM center and the distance between two adjacent PMs, based on the difference between PMC(x,y) and PMC(0,0). Once d/D is known, the energy for this pulse signal and all the other pulse signals corresponding to the same event can be corrected as described hereinabove. It should be noted that the total measured energy of the event is previously determined by adder 40.

As an example of the detrimental of effects of the uncorrected PM distortion in the 6HR system, the uncorrected flood contrast ratio can be up to 2.0.

Correcting the energy of the individual PM 14 at this point in the process by modeling the photomultiplier response greatly reduces the non-linearities in position determination using Anger arithmetic. Alternatively, the energy is corrected by processor 60 immediately after its receipt of the pulse signal.

Once the pulse signals are integrated and, optionally distortion corrected, they are passed in sequence to processor 60 as components of a single radiation event response (a meta-pulse signal). A sequencer 30 synchronizes and sequences the signals from detector circuits 34 to processor 60.

FIG. 5 is a simplified block diagram of processor 60 which forms a nuclear medicine image based on detected radiation events. Since the image is formed by event, the first step performed by processor 60 is to determine the location of the radiation event in detector crystal 41. A preferred method of event location is called Anger arithmetic and is described in U.S. Pat. No. 3,011,057. However other methods of localization are well known and useful in carrying out the invention, for example, as described in U.S. Pat. No. 5,265,072. The disclosures of both Patent documents are incorporated herein by reference.

In order to reduce noise and attain high precision using Anger arithmetic, only relatively strong PM signals are used. A selector 62 selects only those PM signals which are greater than a threshold. Preferably, the height of the threshold is controlled by controller 100 responsive to the total energy (sum of all the signals from adder 40).

As part of the Anger arithmetic, the selected signals are normalized to the sum of the signals generated by all the PMs by a normalizer 68. A positioner 80 calculates the position of the radiation event in detector 41, using Anger arithmetic, based on the selected signals.

The location of the event is now determined. However, if the energy of the event is outside of an energy window, the event is determined to be erroneous and discarded. similar events may have different acquired energies due to system distortions. Thus, an energy corrector 70 corrects the energy of the acquired event for these distortions before windowing. Alternatively, window is varied as a function of the position of the event.

Among the causes for energy distortions are:
(a) PM related non-linearities, which are preferably at least partially corrected in a previous step by PM modeling;
(b) spaces between adjacent PM's 14, which allow some of the energy of the event to escape undetected;
(c) local imperfections in FMS 14 and in detector crystal 41; and
(d) events near the edges of detector crystal 41, wherein some of the energy of the events escapes undetected.

Correcting energy distortions is usually accomplished by calibrating the system to determine calibration data which is stored in a look-up table. When correcting, the exact energy value is determined by interpolating between table values. Preferably, different look-up tables are used depending on the energy range of the radiation event.

In Anger arithmetic, errors in event energy determination at the PM level are translated to errors in positioning of the event. Thus, after energy correction and windowing, a linearity corrector 72 corrects errors in the localization of radiation events. Preferably, a configuration map which maps the linearity errors is used to correct event positions in real-time. Preferably, a continuous approximation such as a spatial B-spline approximation is used to interpolate between map data points. Preferably, different linearity correction maps are used depending on the energy range of the radiation event.

Since different portions of detector crystal 41 have different sensitivities to gamma radiation, an event which occurs in a less sensitive area represents a higher concentration of radio-nuclides than an event which occurs in a, more sensitive area. A sensitivity corrector 74 applies this logic by assigning a weight to each event. A high weight is attached to an event which is detected in a less sensitive, low probability area and a low weight is attached to an event which is detected in a more sensitive, high probability area. Preferably, decay of the injected radio-pharmaceutical is corrected for by varying the weight given to each event.

Energy corrector 70, linearity corrector 72 and sensitivity corrector 74 may be applied in other orders than those described above, with appropriate changes to the correction algorithms.

After being corrected, the event is ready for projection onto the image plane. A geometric transformer 76 applies three types of transformations to the event. First, any additional geometric distortions are corrected, as described in further detail below. Second, static transformations such as zooming and rotating are performed. Third, if detector 41 is moving relative to patient 40, (e.g. detector 41 is rotating around patient 40) the event is transformed to its proper, time dependent position in the image plane. Each transformed event is binned to a location in the image plane and individual event characteristics are lost. It should be noted that the image plane might have three or more dimensions.

A frame builder 78 transforms the events binned in the image plane into a nuclear medicine image. If a three-dimensional image is acquired, frame builder 78 generates a tomographic image from the data binned in the image plane. Frames created by frame builder 78 are then shown on display 92 (FIG. 3).

In a preferred embodiment of the present invention, corrections performed by energy corrector 70, linearity corrector 72, sensitivity corrector 74 and geometric transformer 76 are performed in an event by event basis, such that each event has individualized transformations and/or corrections applied to it. In addition, each correction and transformation can be performed independently. In some prior art systems, geometric transformations were combined to form a single static transformation, which was applied in a single calculation step. Applying transformations on an event by event basis has several advantages, including:

(a) it is more precise to transform a floating point event position than a fixed point matrix position;

(b) each event receives a individualized transformation based on its exact characteristics; and (c) changes in operating parameters, such as changing the zoom factor, does not require recalculation of all of the geometric transformations and corrections, as was the case in prior art systems.

In a preferred embodiment of the invention, the corrections are performed in the following manner:

(a) the positioning system outputs a 14 bit fixed value for the location of the event;

(b) the 14 bit value is converted to a 20 bit value by adding 6 random LSB (least significant bits) thereto;

(c) the 8 MSB (most significant bits) are used to retrieve four gridpoints of a coarse linearity correction map, each gridpoint has a 24 bit floating point value;

(d) the event location is corrected using bi-linear interpolation of the four gridpoints, resulting in a 24 bit floating point value; and (a) the transformations and such are applied to the resulting floating point event location.

In a further preferred embodiment of the present invention, Compton scattering artifacts are reduced in real-time. A preferred method of Compton scattering artifacts reduction is described in U.S. Pat. No. 5,293,195, the disclosure of which is incorporated herein by reference. To reduce Compton scattering artifacts, each event is added to the image plane with a calculated weight. Pixels surrounding the event location are also incremented with various weights. Compton artifact reduction is preferably performed by a Compton remover 77.

It should be appreciated that all of the above described corrections and transformations can be changed during processing responsive to input from an operator or other sources of information. For example, if one frame acquisition time is found to be shorter than another frame acquisition time, the events in the shorter frame are given a higher weight.

In another preferred embodiment of the present invention, an event counter is used to count the approximate number of real events. If a lower number of radiation events is processed by system 61, due to count rate limitations, the weight of processed events is increased to compensate.

In yet another preferred embodiment of the present invention, a parallel beam image is simulated using a fan beam collimator by applying a geometric transformation to each event. Parallel beam simulation is useful when a fan beam collimator is used to acquire an image of a small organ, but it is desirable to view an undistorted image which utilizes the image plane more efficiently. As noted above, the image plane has a limited spatial resolution, to best utilize it, the region of interest should fill up as much of the image plane as possible. To effect this simulation, an organ is imaged using a fan beam collimator. Each event is transformed by geometric transformer 78 to correct for the distortions caused by the fan beam collimator. It should be noted that this transformation is applied before tomegraphic processing of the events, in the frame builder 78.

In a further preferred embodiment of the present invention, variable mechanical misalignments are corrected in real-time.

In some imaging procedures, detector 41 is moved along an axis of patient 40. If the speed of motion is not constant, portions of patient 40 which are scanned faster appear have less events than portions which are scanned more slowly. In a preferred embodiment of the present invention, each event is given a weight depending on the actual speed of the scanning; a higher weight for fast scanning and a lower weight for slow scanning.

Figure 7:
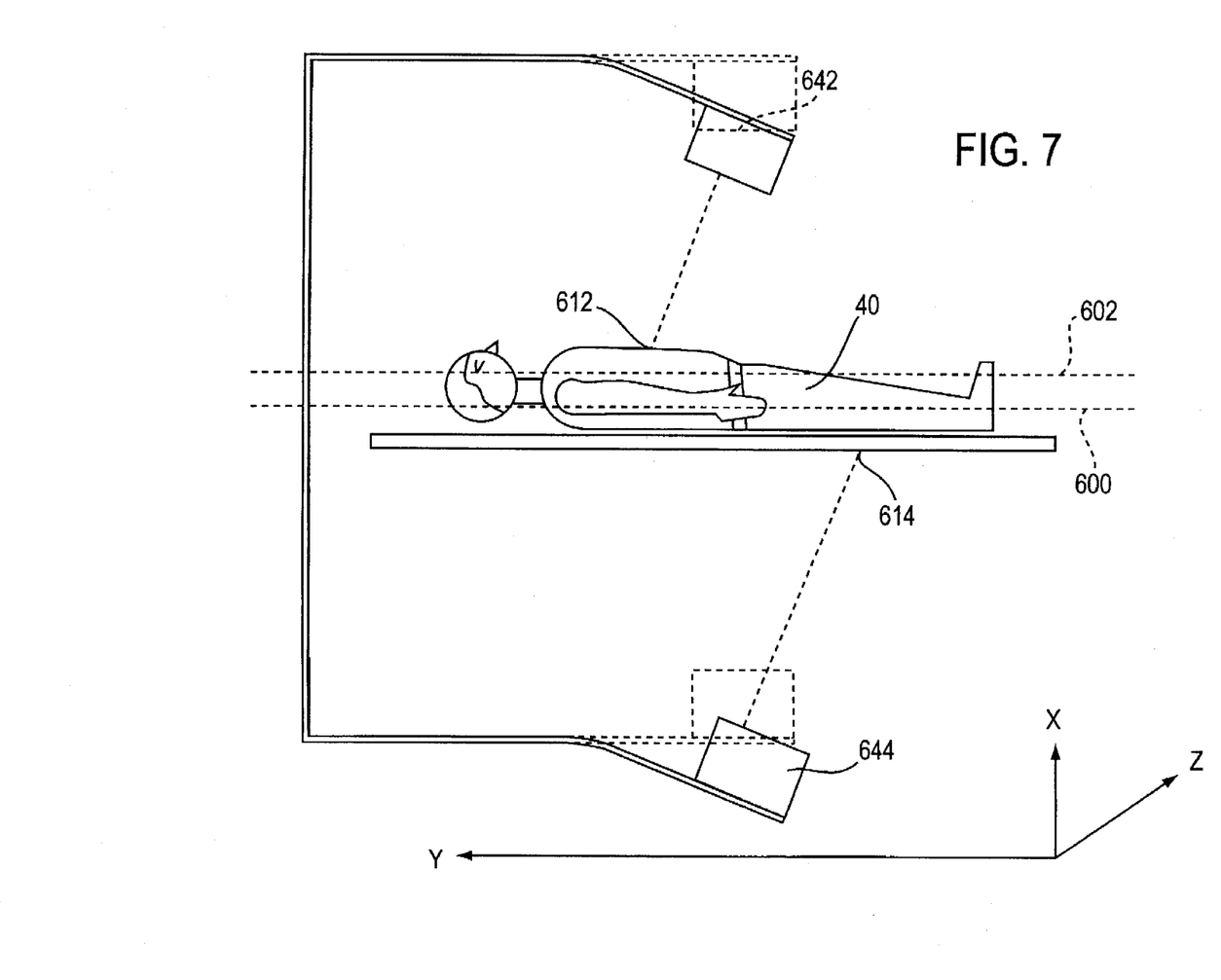
FIG. 7 shows the effect of sagging on a detector crystal imaging a patient.

FIG. 7 shows another type of mechanical misalignment. Patient 40 has a Y axis along his body and an X-Z plane bisecting it. A nuclear camera 642 is rotated around patient 40, to capture events for forming a tomographic image. A first misalignment is y-axis rotation misalignment. Due to the great weight of camera 642, an actual center of rotation 602 is different from a configured center of rotation 600. In addition, camera 642 sags either towards or away from the center of rotation as a function of the rotation angle. This misalignment is corrected in a preferred embodiment of the present invention by applying an angle dependent geometric transformation, to each event so that it is moved in the X-Z plane. This transformation is applied by geometric transformer 76.

A second misalignment is axial (line of sight) miss-registration As mentioned above, camera's 642 weight causes it to sag. However, when camera 642 is above patient 40, it sags towards him and when a nuclear medicine camera 644 is below him, it sags away from him. Since, the cameras ore mounted on long beams, which bend so that the cameras viewing angle changes, the line of sight of the camera moves along the Y-axis of patient 40 as the amount of sagging changes. In a preferred embodiment of the present invention, this misalignment is corrected by applying an angle dependent geometric transformation to each event so that it is moved along the Y-axis.

Mechanical misalignments are typically detected either by configuration data, by feedback from mechanical position, velocity or acceleration sensors, or by processing the acquired data to find correlations and Fourier frequency peaks which correspond to certain types of misalignments. For example y-axis rotation misalignment (described above). Manifests itself as a Fourier frequency peak which corresponds to the degree of misalignments.

In yet another preferred embodiment of the invention geometric transformations applied to an event are dependent on a measured biological rhythm, such as stomach contractions, breathing or heart beat.

It should be noted that all of the abovementioned corrections are preferably done in real-time on an event by event basis. Performing calculations on individual events in real-time produces high accuracy results without the data-storage penalty required if all the events are stored for off line processing.

It should be appreciated that a look-up-table and a mathematical formula can sometimes be interchanged with respect to function. However, a mathematical function is inherently more precise than a look-up-table, albeit, slower and not as capable of being recalibrated.

It should also be appreciated that processor 60, as described herein can be used with an analog front end, not only with a digital front end as described.

It will be appreciated by persons skilled in the art that the present invention is not limited to what has been thus far described. Rather, the scope of the present invention is limited only by the following claims:

We claim:

1. A method of acquiring an analog electrical pulse signal caused by a radiation event impinging on a detector crystal and viewed by a plurality of detector units, for forming an image based on a plurality of said events, each of which is captured by some of said detector units, comprising:

adding a linearity enhancement signal to said analog signal; and converting said analog signal, after adding said linearity enhancement signal, to a digital signal, wherein, said linearity enhancement signal is slowly varying relative to a duration of a pulse in said analog signal and wherein said linearity enhancement signal enhances the linearity of said analog to digital conversion.

2. A method according to claim 1, further comprising digitally subtracting a value equivalent to the value of the linearity enhancement signal at said conversion from the digital signal.

3. A method of acquiring an analog electrical pulse signal caused by a radiation event impinging on a plurality of detector units, for forming an image based on a plurality of said events, each of which is captured by some of said detector units, comprising:

adding a resolution enhancement signal to said analog signal; and converting said analog signal, after adding said resolution enhancement signal, to a digital signal, wherein, said resolution enhancement signal is fast varying relative to a duration of a pulse in said analog signal and wherein said resolution enhancement signal enhances the resolution of said analog to digital conversion.

4. A method according to claim 3, further comprising adding a linearity enhancement signal to said analog signal, wherein said linearity enhancement signal is slowly varying relative to the duration of said pulse and wherein said linearity enhancement signal enhances the linearity of said analog to digital conversion.

5. A method according to claim 3, wherein said resolution enhancement signal is synchronized to said analog to digital conversion.

6. A method according to claim 3, wherein said resolution enhancement signal is synchronized to the integration cycle.

7. A method according to claim 6, wherein the sum of the contribution of said resolution enhancement signal over a time period of one integration has a known value.

8. A method according to claim 7, wherein said value is zero.

9. A method according to claim 2, further comprising digitally subtracting a value equivalent to the value of the resolution enhancement signal at said conversion from the digital signal.

10. A method for correcting and transforming acquired radiation events on an event-by-event basis, comprising:

(a) correcting a radiation event for at least one of linearity, energy and/or sensitivity errors;

(b) geometrically transforming said radiation event, in an independent manner from (a), wherein said geometrical transforming is not related to linearity correction; and (c) assigning said corrected and transformed radiation event to a position in a matrix.

11. A method according to claim 10, wherein said correcting is time-dependent.

12. A method according to claim 11, wherein said correcting corrects for a decay of a radioactive source which produces said event.

13. A method according to claim 11, wherein said correcting corrects for metabolizing of a radioactive source which produces said event.

14. A method according to claim 10, wherein said correcting is dependent on an orientation of a detector used to acquire said radiation event relative to a radiation source which generates said radiation event.

15. A method according to claim 10, wherein said correcting is dependent on an external variable.

16. A method according to claim 10, wherein said correcting is dependent on biological rhythms of a patient which is being imaged using said radiation event.

17. A method according to claim 16, wherein said biological rhythm is a heart rhythm.

18. A method according to claim 16, wherein said biological rhythm is a breathing rhythm.

19. A method according to claim 16, wherein said biological rhythm is a stomach rhythm.

20. A method according to claim 10, wherein said correcting is dependent on the energy of the event.

21. A method according to claim 10, wherein said geometric transforming is time-dependent.

22. A method according to claim 10, wherein said geometric transforming is dependent on a orientation of a detector used to acquire said radiation event relative to a radiation source which generates said radiation event.

23. A method according to claim 22, wherein said detector rotates around said radiation source and wherein said geometric transformation corrects for axial misalignments.

24. A method according to claim 22, wherein said detector rotates around said radiation source and wherein said geometric transformation corrects for angular axial misregistration.

25. A method according to claim 10, wrerein said geometric transforming is dependent on a velocity of a detector used to acquire said radiation event relative to a radiation source which generates said radiation event.

26. A method according to claim 25, wherein said detector moves in parallel to said radiation source.

27. A method according to claim 10, wherein said geometric transforming is dependent on an external variable.

28. A method according to claim 10, wherein said geometric transforming is dependent on biological rhythms of a patient which is being imaged using said radiation event.

29. A method according to claim 28, wherein said biological rhythm is a heart rhythm.

30. A method according to claim 28, wherein said biological rhythm is a breathing rhythm.

31. A method according to claim 28, wherein said biological rhythm is a stomach rhythm.

32. A method according to claim 10, wherein said geometric transforming is dependent on the energy of the event.

33. A method according to claim 10, wherein said geometric transformation corrects for distortions caused by a collimator used to acquire said radiation event.

34. A method according to claim 32, wherein said geometric transformation transforms an event which was acquired using a fan-shaped collimator into an event which appears to have been acquired using a parallel collimator.

35. A method for transforming acquired radiation events on an event-by-event basis, comprising:

geometrically transforming a radiation event, in a manner independent from and unrelated to linearity correction; and assigning said transformed radiation event to a position in a matrix.

\* \* \* \* \*